United States Patent [19]

Fritz et al.

[11] 4,272,246

[45] Jun. 9, 1981

[54] METHOD AND APPARATUS FOR CHROMATOGRAPHIC QUANTITATIVE ANALYSIS

[75] Inventors: James S. Fritz; Douglas T. Gjerde, both of Ames, Iowa; Gabriella Schmuckler, Haifa, Israel

[73] Assignee: The United States of America as represented by the United States Department of Energy, Washington, D.C.

[21] Appl. No.: 67,855

[22] Filed: Aug. 20, 1979

[51] Int. Cl.³ ..................... G01N 31/04; G01N 27/08
[52] U.S. Cl. ............................. 23/230 R; 23/230 M; 210/198.2; 210/656; 422/70
[58] Field of Search ........................ 23/230 R, 230 M; 422/70; 210/25, 31 C, 198 C

[56] References Cited

U.S. PATENT DOCUMENTS

| | | | |
|---|---|---|---|
| 3,847,550 | 11/1974 | Scott et al. | 422/70 |
| 3,920,397 | 11/1975 | Small et al. | 23/230 R |
| 4,070,284 | 1/1978 | Fujita et al. | 210/31 C |

OTHER PUBLICATIONS

Rohm & Haas Co.; Amber-hi-lites, No. 159 8(1978).

Primary Examiner—Michael S. Marcus
Attorney, Agent, or Firm—James W. Weinberger; Frank H. Jackson; James E. Denny

[57] ABSTRACT

An improved apparatus and method for the quantitative analysis of a solution containing a plurality of anion species by ion exchange chromatography which utilizes a single eluent and a single ion exchange bed which does not require periodic regeneration. The solution containing the anions is added to an anion exchange resin bed which is a low capacity macroreticular polystyrene-divinylbenzene resin containing quarternary ammonium functional groups, and is eluted therefrom with a dilute solution of a low electrical conductance organic acid salt. As each anion species is eluted from the bed, it is quantitatively sensed by conventional detection means such as a conductivity cell.

5 Claims, 4 Drawing Figures

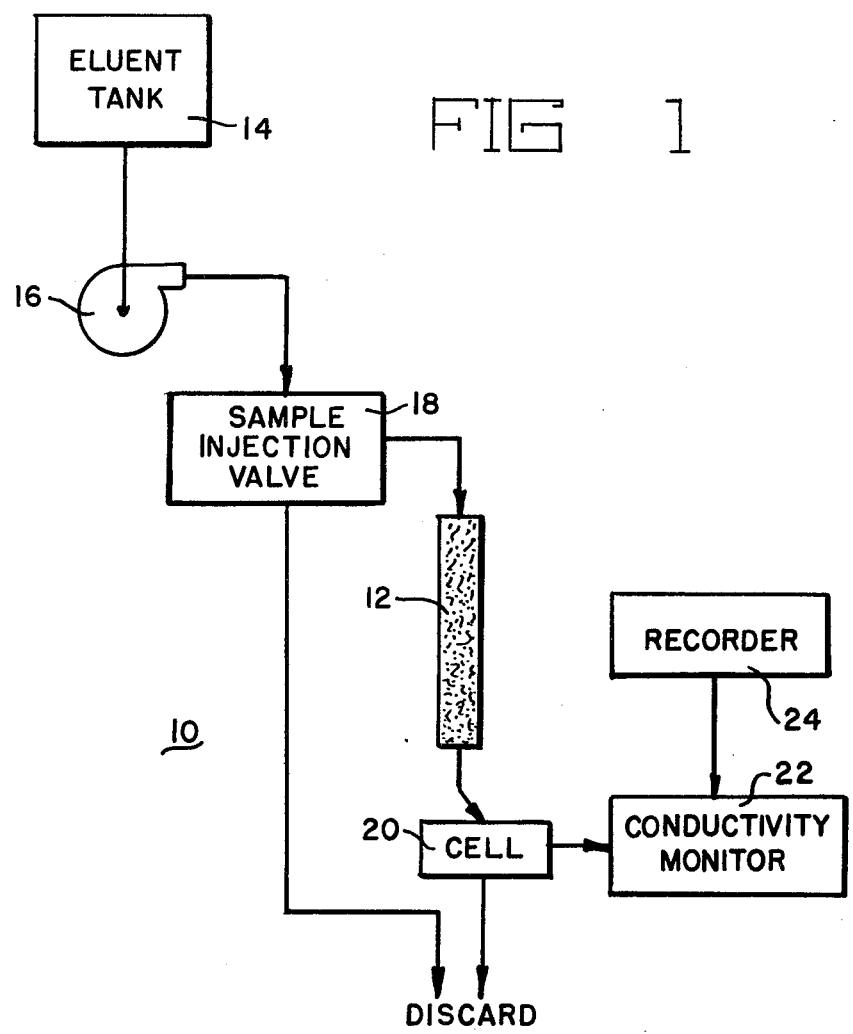

METHOD AND APPARATUS FOR CHROMATOGRAPHIC QUANTITATIVE ANALYSIS

CONTRACTUAL ORIGIN OF THE INVENTION

The invention described herein was made in the course of, or under, a contract with the UNITED STATES DEPARTMENT OF ENERGY.

BACKGROUND OF THE INVENTION AND PRIOR ART

This invention relates to a method and apparatus for the quantitative analysis of a solution containing a plurality of anions by ion exchange chromatography.

Ion exchange chromatography has developed in recent years into a widely used analytical technique for the simultaneous quantitative analysis of mixtures of organic or inorganic anions and cations, or for the separation of chemical compounds that can be converted to an anionic or cationic form. In this technique the solution mixture to be analyzed is introduced into a column containing an ion exchange resin, and the different ions are subsequently eluted therefrom by a suitable eluent, viz. an ionic solution specifically selected for the purpose. The different anions or cations emerge from the ion exchange column at different times which are specific for each anion or cation. The retention times are recorded on a chart using automatic detection. The difference in signal between the eluent background and the anion or cation will produce peaks which are directly related to the concentrations of the anions or cations present in the sample solution.

The application of ion exchange chromatography for the separation and simultaneous quantitative analysis of mixtures of inorganic anions, such as halides, sulfates, phosphates, nitrites, nitrates, etc., as well as of cations, such as the alkali and alkaline earth metal ions, has been severely limited by lack of a suitable detector. However, many of these problems were solved by U.S. Pat. No. 3,920,397 which issued on Nov. 18, 1975. This patent describes a method and apparatus for chromatographic quantitative analysis of ionic species in solution. The solution to be analyzed is first passed into a separator ion exchange resin bed where chromatographic separation of the ions is carried out using a developing reagent or eluent. The eluted ions are then passed through a suppressor or stripper ion exchange resin bed where the developing reagent eluent is acted upon by the ion exchange resin so that it does not reach the detector in highly ionized form along with the separated ion species being analyzed. This step is necessary to prevent the high conductance of the ions in the eluent from "swamping" the much lower conductance of the separated ions to be measured. For example, the developing reagent is converted to a weakly dissociated molecule such as water or is captured on ion exchange sites. The low conductance eluent along with the separated ions is then passed through a detector such as a conductivity cell which can now measure the conductivity of the separated ion species and which provides a signal to associated readout means for preparing a permanent record.

The instruments have found wide acceptance and are used for the detection and accurate determination of anionic and/or cationic admixtures down to the trace level. Many uses are described in *Ion Chromatographic Analysis of Environmental Pollutants* edited by Sawicki, Mulik and Wittgenstein, Ann Arbor Science Publishers Inc., 1978. However, the instruments do suffer from various disadvantages mainly due to the need for suppression. For example, the large dead volume of the suppressor column requires the use of rather large volumes of solutions. The quality of the signal from the conductometric detection system is dependent upon the degree of exhaustion of the suppressor column during regeneration of the suppressor column. The regeneration cycle introduces high conducting electrolytes into the system which require more eluent pumping time to stabilize the system baseline. The chemical composition of the regenerants are acids or bases necessitating that the column, tubing and valves be of material which is corrosion resistent. The analysis of strongly retained anions requires a higher concentration of eluents which causes the suppressor columns to exhaust more rapidly.

SUMMARY OF THE INVENTION

An improved apparatus and method for the ion exchange chromatographic quantitative analysis of anions has been developed which eliminates many of the difficulties enumerated above. The apparatus of the invention utilizes a new, low capacity anion exchange resin which permits the use of dilute solutions of low electrical conductance salts as eluents, thus eliminating the necessity for suppressor columns and the problems attendant with the use of such columns. Accordingly, the apparatus for the quantitative analysis of a solution containing a plurality of anion species consists of an anion exchange resin bed for chromatographically separating the plurality of anion species by elution through the bed, the bed being a low capacity, polystyrene-divinylbenzene macroreticular anion exchange resin containing quarternary ammonium functional groups, means for adding a plurality of anions in solution to the anion exchange resin bed, means for adding an eluent solution to the anion exchange resin bed for separating the anion species and eluting the anions separately from the bed and means for quantitatively detecting each separated anion species of interest as it is eluted from the resin bed. The method of the invention includes not only the use of the low capacity anion exchange resin described hereinbefore but also the use of an eluent which is a dilute solution of a low electrical conductance organic acid salt.

The invention has several advantages over the prior art method and apparatus. The chemical composition of the anion exchange resin bed is different from prior art resin beds and is not as susceptible to chemical destruction and as sensitive to the pH of the eluent as other resins. The eluents used in the present invention are very efficient in resolving anions that are normally strongly retained on the analytical column. These eluents have low conductance ($<10^{-4}$mho/cm) and need not be processed through suppressor columns. Since no suppressor columns are needed the regeneration step is completely eliminated and the apparatus can operate for long periods without interruption. Baseline restabilization is not necessary because the apparatus works continuously without interruption. Finally, the apparatus is much simpler to construct and requires less tubing and valves since the suppression columns are eliminated.

It is therefore one object of the invention to provide a low capacity anion exchange resin from which anions can be separated and eluted using a low conductance eluent.

It is another object of the invention to provide a method for making a low capacity anion exchange resin.

It is another one object of the invention to provide an improved method and apparatus for the quantitative analysis of solutions containing a plurality of anion species.

It is still another object of the invention to provide a method and apparatus for the chromatographic quantitative analysis of a solution containing a plurality of anion species which does not require the use of a suppressor column.

Finally it is the object of the invention to provide an improved method and apparatus for the chromatographic quantitative analysis of a solution containing a plurality of anion species which utilizes a low capacity anion exchange resin for separating the anion species which permits the use of eluents having low electrical conductance.

BRIEF DESCRIPTION OF THE DRAWINGS

FIG. 1 is a schematic representation of the apparatus of the invention.

DETAILED DESCRIPTION OF THE INVENTION

Figure 4:
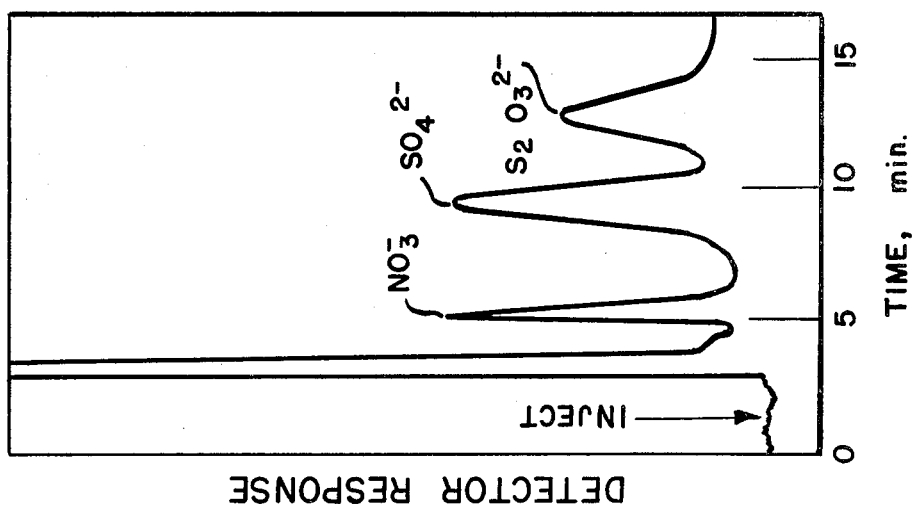
FIG. 4 is a chromatogram showing the separation of 24.4 ppm nitrate, 22.0 ppm sulfate and 21.3 ppm thiosulfate from XAD-1 resin having 0.04 meq/g using $5 \times 10^{-4}$ M ammonium o-sulfobenzoate at pH 7.3.

These and other objects of the invention for the quantitative analysis of a plurality of anion species in a solution may be met by adding the solution containing the anions to an anion exchange resin bed which contains a polystyrene-divinylbenzene macroreticular anion exchange resin containing quarternary ammonium functional groups and having an ion exchange capacity in the range of 0.04 to 0.007 milliequivalents per gram of resin (meq/g), passing an eluent through the resin bed to chromatographically separate the anion species and elute the separated anion species individually from the resin bed, the eluent being a dilute solution of a low electrical conductance organic acid salt, and passing the eluent containing the individual anion species into a conductivity cell which produces an electrical signal proportional to the amount of anion species present in the cell.

Referring now to FIG. 1, the apparatus 10 of the invention comprises an ion exchange column 12 containing a low capacity anion exchange resin for chromatographically separating a plurality of different anion species into groups of a single species, a tank 14 for storing eluent and a pump 16 for supplying eluent to column 12. A sample injection valve 18 is interspaced between pump 16 and column 12 for introducing a sample solution containing the anion species to be analyzed into the apparatus. The eluent leaving column 12 passes into a conductivity cell 20 where fluctuations in anion concentration produce an electrical signal which is proportional to the amount of anion material and which is directed to conductivity monitor 22. The electrical signal of the conductivity monitor 22 is then directed to a recorder 24 which provides a visible record. The conductivity monitor 22 and the recorder 24 together constitute readout means for the signal from the conductivity cell 20.

The capacity of the anion exchange resin in column 12 may vary from 0.2 to 0.001 meq/g while the range is preferably from 0.04 to 0.007 meq/g. The resin is prepared from macroreticular cross-linked polystyrene-divinylbenzene polymer adsorbents which have an average pore diameter of from about 50 to about 210 Å and a surface area ($m^2$/gm) of from about 100 to about 800. Such polymers are marketed by Rohm and Haas Company, Philadelphia, Pa. as beads under the trademarks XAD-1, XAD-2 and XAD-4. The beads are preferably in the particle size range of about 100 to about 400 mesh (U.S. Sieve Size). The anion exchange resin is prepared by chloromethylating the beads by contacting the beads at room temperature with a solution of chloromethylmethyl ether diluted with methylene chloride and nitromethane and catalyzed with zinc chloride for from about 5 to 15 minutes until the desired degree of chloromethylation is attained and then quenching the reaction with water. The beads are then dried and contacted with liquefied trimethylamine until completely aminated. A methylation solution which has been found exceptionally suitable consists of about 10 parts by volume of chloromethylmethyl ether, about 10 to 50 parts by volume methylene chloride and 3 parts by volume of nitromethane which together with about 1 part by weight of zinc chloride as a catalyst, will methylate about 3 parts by weight of beads. Resins having a capacity of from about 0.02 to about 0.001 meq/g can be prepared by this method. The capacity is controlled by varying the chloromethylation reaction time and by varying the volume of methylene chloride and the zinc chloride catalyst. With the information which has been given, more precise conditions for preparing the anion exchange resins having a particular capacity can readily be determined by those skilled in the art with a minimum of experimentation.

The eluent is an aqueous solution of a substance that ionizes to give a cation and an anion. Typically the eluent cation has been potassium, although other alkali metal cations such as sodium can be used. Ammonium, alkylammonium, or other organic ammonium ions can also be used. The eluent anion must be one that is retained rather strongly by the anion-exchange resin so that a very low concentration of the eluent salt will move anions to be separated along the chromatographic ion-exchange column. The conductance of the eluent ions must be sufficiently low so that the separated anions, each with an appropriate cation counter ion, will give a detection signal well above that of the eluent background. Generally a conductance of less than about $10^{-4}$ mho/cm has been found satisfactory.

Suitable eluents are dilute solutions of low electrical conductance organic acid salts. These include potassium acid phthalate, potassium benzoate, potassium o-sulfobenzoate and potassium o-nitrophenol. Suitable concentrations may vary from about $1 \times 10^{-5}$ M to about $5 \times 10^{-4}$ M. The pH values may vary from about 5 to about 9 depending upon the salt. The pH value should be one which will permit most of the eluent to be present in the anion form rather than in the molecular acid. A pH that is too alkaline is to be avoided because it may raise the background conduction.

The following examples are given merely as illustrative of the method and apparatus of the invention and are not to be taken as limiting the scope of the invention which is defined by the appended claims.

EXAMPLE I

To prepare an anion-exchange resin of approximately 0.04 to 0.07 meq/g capacity, 3.0 g of XAD-1 resin (150–325 mesh particle size) was mixed with 10 ml of chloromethyl methyl ether, 11 ml of methylene chloride, 3 ml of nitromethane, and 3.0 g of zinc chloride. The chloromethylation reaction was allowed to proceed for 5 to 15 minutes at room temperature, then quenched and the resin washed with water. Varying the reaction time makes it possible to obtain a final resin of varying ion-exchange capacity. The chloromethylated resin is aminated by adding liquid trimethylamine and allowing it to evaporate overnight. Resin of a still lower capacity can be prepared by increasing the volume of methylene chloride and reducing the amount of catalyst used. For example, a resin of 0.007 mq/g final capacity was prepared as above but increasing the methylene chloride to 40 ml and using only 1.0 g of zinc chloride.

EXAMPLE II

The chromatographic apparatus as shown in FIG. 1 was set up which consisted of: A Milton Roy pump (Model 376 Simplex) which serves to force the eluent to flow from the eluent tank through the sample loop, the analytical column, and the conductivity cell, at a flow rate of about 2 ml/min; a sample injection value which makes use of a sample loop and enables liquid increments as small as 50–100 microliters to be injected; an analytical separation column, containing the low capacity resin made as described in Example I, which is about 2 mm internal diameter and 1000 mm long and containing about 1 gm of resin, and a 10 ml dead volume conductivity cell used to measure the conductivity. A Dionex ® conductivity detector was used to continuously monitor the conductivity of the effluent while a Fisher Recordall strip chart recorder was used to produce a record of the output of the conductivity meter.

Solutions containing mixtures of 2 or 3 different anions were passed through a column. The anions were then eluted with several different elements.

Potassium acid phthalate, pH 4.4, $5.0 \times 10^{-4}$ M was the first eluent tried. It gave well-defined peaks for separation of simple mixtures of two or three common anions using a low-capacity (0.04 meq/g) XAD-1 resin column and a conductance detector. Further investigation revealed that $5.0 \times 10^{-4}$ M solutions of potassium benzoate, potassium phthalate, and potassium o-sulfobenzoate (all at pH6) are excellent eluents. A $6.5 \times 10^{-5}$ M solution of potassium malonate, pH6.1, is a much less effective eluent than any of the three listed above. Apparently a benzene ring in the chemical structure of the eluent salt plays a major role in enabling inorganic anions to be effectively eluted from the XAD-1 resin. Similarly, a $5.0 \times 10^{-4}$ M solution of potassium perchlorate or potassium citrate was a rather ineffective eluent. Adjusted retention times for elution of inorganic anions with various eluents are summarized in Table I. Several experiments indicated that there is little difference in effectiveness between the potassium and sodium salts of the different eluents.

TABLE I

| | Adjusted retention times (min) of anions on XAD-1, 0.04 neg/g with different eluents (to = 1.8 min) | | | | | |
|---|---|---|---|---|---|---|
| Eluent Ion | benzoate $5 \times 10^{-4}$ M, pH = 6.0 | phthlalate $5 \times 10^{-4}$ M, pH = 4.4 | phthalate $5 \times 10^{-1}$ M, pH = 6.1 | sulfobenzoate $5 \times 10^{-4}$ M, pH = 5.8 | perchlorate $5 \times 10^{-4}$ M, pH − 7.0 | malonate $6.5 \times 10^{-4}$ M, pH = 6.1 |
| $F^-$ | 2.8 | 0.8 | 0.0 | 0.0 | — | — |
| $Cl^-$ | 3.9 | 1.3 | 0.7 | 0.7 | 5.8 | 4.2 |
| $NO_2^-$ | 4.8 | 1.4 | 0.8 | 1.3 | — | 3.8 |
| $Br^-$ | 6.3 | 2.1 | 1.3 | 1.1 | 8.6 | 4.6 |
| $NO_3^-$ | 7.2 | 2.2 | 1.4 | 1.3 | 9.4 | 6.7 |
| $SO_4^=$ | | 16.4 | 4.4 | 3.3 | | |
| $I^-$ | | 6.3 | 5.4 | | | |
| $SCN^-$ | | 14.7 | 15.0 | | | |
| $C_2O_4^=$ | | | 5.0 | 3.5 | | |
| $CrO_4^=$ | | | 0.8 | 0.5 | | |
| $SO_3^=$ | | | 4.5 | 3.2 | | |
| $S_2O_3^=$ | | | 7.5 | 5.1 | | | negative or multiple peak very long rentention times

Figure 2:
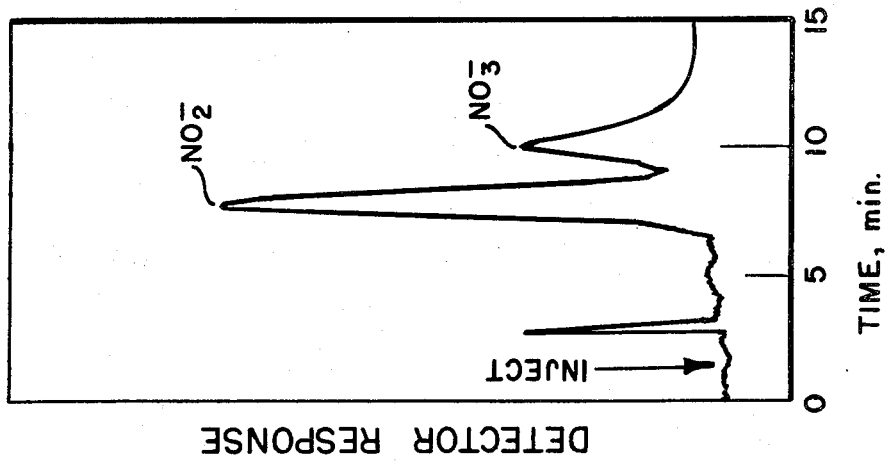
FIG. 2 is a chromatogram showing the separation of 16.0 ppm nitrite and 12.2 ppm nitrate from XAD-1 resin having 0.04 meq/g using $6.5 \times 10^{-4}$ M potassium benzoate eluent at pH 5.0.

Of the three eluents, potassium benzoate has the mildest eluting ability. Using 0.04 meq/g XAD-1 resin and $5.0 \times 10^{-4}$ M benzoate, an excellent separation of fluoride chloride and bromide was obtained. FIG. 2 shows excellent resolution in separating nitrate and nitrite anions using the benzoate eluent. However, benzoate is not an effective eluent for ions that are more tenaciously held by the XAD-1 resin, such as sulfate, iodide and thiocyanate.

Figure 3:
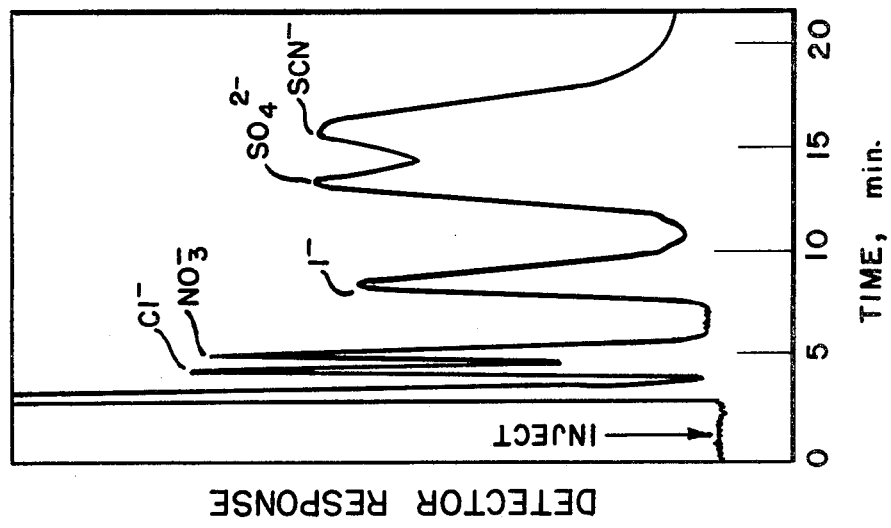
FIG. 3 is a chromatogram showing the separation of 5.1 ppm chloride, 12.2 ppm nitrate, 39.0 ppm iodide, 44.1 ppm sulfate and 28.6 ppm thiocyanate from XAD-1 resin having 0.04 meq/g using $6.5 \times 10^{-4}$ M potassium phthalate at pH 4.4.

Phthalate is intermediate in eluting ability of the three eluents. Using a $5.0 \times 10^{-4}$ M solution, anions are eluted more quickly when the eluent pH is raised from 4.4 to 6.1 (see Table I). For sulfate the pH effect is quite dramatic, the adjusted retention time going from 16.4 min at pH 4.4 to only 4.4 min at pH 6.1. However, thiocyanate has almost the same adjusted retention time at the two pH values (14.7 min and 15.0 min). The retention time of iodide changes only slightly with pH. Since more of the phthalate is present as the divalent anion at pH 6.1, it would be expected to be a better eluent at the higher pH. The background conductivity is greater at pH 6.1, making the anion peak heights lower. FIG. 3 shows a chromatogram for a mixture containing five different anions.

Ammonium o-sulfobenzoate, pH 5.8, was the most effective salt for eluting divalent anions, which are usually very strongly retained on the resin. The adjusted retention time of the chromate ion, for instance, is only 0.5 min on the 0.04 meq/g XAD-1 resin using $5.0 \times 10^{-4}$ M sulfobenzoate. This retention time compares very favorably with the 25 min retention time obtained in the prior art system using a mixture of sodium bicarbonate and sodium carbonate as the eluent. The retention time of the oxalate anion is 3.5 min with sulfobenzoate benzoate and XAD-1 anion exchange resin, compared with 18 min in the prior art system. The separation of sulfate and thiosulfate is shown in FIG. 4 with o-sulfobenzoate at pH 7.3 as the eluent.

EXAMPLE III

Macroporous resins of three differing capacities were loaded with several anions at a time and eluted with potassium acid phthalate to show that the concentration of an anionic eluent required to elute any given anion from a resin column decreases with decreasing resin capacity. The data is given in Table II below which compares the adjusted retention times of a number of anions from resin columns of different components.

TABLE II

| | Comparative adjusted retention times (min) for XAD-1 0.04 meg/g, XAD-1 0.07 meg/g, and XAD-1 0.007 meq/g | | |
|---|---|---|---|
| Iron | 0.07 meq/g* | 0.04 meq/g* | 0.007 meq/g+ |
| $F^-$ | 0.6 | 0.0 | 0.6 |
| $Cl^-$ | 1.5 | 0.7 | 1.0 |
| $NO_2^-$ | 2.0 | 0.8 | 1.4 |
| $Br^-$ | 3.8 | 1.3 | 1.2 |
| $NO_3^-$ | 4.5 | 1.4 | 1.5 |
| $SO_4^{2-}$ | 11.5 | 4.4 | 5.5 |
| $I^-$ | | 5.4 | 2.0 |
| $CNS^-$ | | 15.0 | 4.0 |
| $C_2O_4^{2-}$ | 12.8 | 5.0 | 5.7 |
| $CrO_4^{2-}$ | 1.3 | 0.8 | 3.4 |
| $SO_3^{2-}$ | 11.6 | 4.5 | 5.8 |
| $S_2O_3^{2-}$ | | 7.5 | 8.1 |

*Eluent: $5 \times 10^{-4}$ M KHP, pH = 6.0 to = 1.8 min
Column: 2 mm I.D. × 1000 mm
+Eluent: $1 \times 10^{-4}$ M KHP, pH = 7.1 to = 1.5 min
Column: 3 mm I.D. × 500 mm The data shows appreciably longer retention times for all anions on the 0.07 meq/g resin compared to the 0.04 meq/g resin. Anions are eluted efficiently from the resin column at the lowest capacity (0.007 meq/g) by a phthalate eluent that is only $1.0 \times 10^{-4}$ M or a benzoate eluent of only $2 \times 10^{-4}$ M. Using eluents of such low conductivity enhances the sensitivity of the system and consequently quantitative much better than for similar separations attempted on a XAD-1 anion-exchange column.

EXAMPLE IV

The quantitative determination of ppm concentrations of sulfate in water is a widely studied problem; often a turbidimetric or spectrophotometric procedure is used for the analysis. Low concentrations of sulfate can be separated rapidly by anion chromatography. Using an appropriate calibration plot, an accurate quantitative determination of the sulfate is possible.

The efficacy of the chromatographic method was demonstrated by separating a series of samples containing chloride, nitrate and sulfate on a 50-cm XAD-1 column with $6.5 \times 10^{-4}$ M potassium phthalate (pH 6.2) as the eluent. The chloride and nitrate concentrations were held constant at 5.12 and 12.2 ppm, respectively, while the sulfate concentration was varied from 2.75 ppm to 13.75 ppm. A plot of sulfate peak height vs. concentration proved to be perfectly linear, so that an accurate quantitative determination of sulfate was possible. The chromatograms obtained point to the possible use of the chromatographic system for routine water analysis for the simulataneous determination of three anions.

EXAMPLE V

A tap water sample was analyzed for bicarbonate. The sample was diluted 10-fold with distilled water and a 100 microliter sample was added to a column containing XAD-1 anion-exchange resin of 0.007 meq/g capacity. On elution with $1.0 \times 10^{-4}$ M potassium benzoate, pH 6.0, a bicarbonate peak preceeded peaks from other anions in the water. Addition of increasing concentrations of bicarbonate to the water sample caused the first peak to increase in height, thus confirming that the peak in the original water sample was indeed bicarbonate. By the "standard addition method", a linear plot of peak height vs. bicarbonate was obtained; the intercept indicated a bicarbonate concentration of 5.2 ppm in the diluted water or 52 ppm of bicarbonate in the original, undiluted water sample.

It has been shown that the method and apparatus of the invention utilizing a column containing a new anion-exchange resin of very low capacity, together with an eluent of low concentration and a conductivity detector is capable of giving quick and accurate separations of mixtures containing several anions.

The embodiments of the invention in which an exclusive property or privilege is claimed are defined as follows:

1. A method for chromatographic quantitative analysis of a plurality of anion species in a solution consisting essentially of
   adding a solution containing a plurality of anion species to a polystyrene-divinylbenzene macroreticular anion exchange resin bed containing quarternary ammonium functional groups, the resin having a capacity of no more than 0.2 millequivalents per grams of resin;
   passing an eluent having a conductance of less than about $10^{-4}$ mho/cm through the resin bed containing the plurality of anion species to chromatographically separate the plurality of anion species on the resin bed and for eluting the separated species individually from the resin bed, the conductivity of the eluent being less than the conductivity of the anion species being eluted; and
   determining the conductivity of each separated anion species exiting from the resin bed, the conductivity being directly proportional the quantity of anion species present in the solution.

2. The method of claim 1 wherein the anion exchange resin has a specific anion capacity in the range of about 0.2 to 0.001 millequivalents per gram of resin.

3. The method of claim 2 wherein the eluent is a dilute solution of an organic acid salt.

4. The method of claim 3 wherein the organic acid salt is an alkali metal or organic ammonium salt selected from the group consisting of acid phthalate, benzoate, o-sulfobenzoate and o-nitrophenol.

5. The method of claim 4 wherein the organic acid salt is present in a concentration of from about $1 \times 10^{-5}$ M to about $5 \times 10^{-4}$ M and the pH of the eluent is between about 5 and 9.

* * * * *